United States Patent [19]

Nakayama

[11] Plant 4,072

[45] July 5, 1977

[54] PEACH TREE

[76] Inventor: Hitoshi P. Nakayama, 7420 E. Lincoln, Fowler, Calif. 93625

[21] Appl. No.: 710,684

[22] Filed: Aug. 2, 1976

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Huebner & Worrel

[57] ABSTRACT

A variety of peach tree the fruit of which ripens about a week to 10 days earlier than the Red Top variety (unpatented) which the new variety most nearly resembles.

3 Drawing Figures

BACKGROUND OF THE INVENTION

Because of the obvious desirability of reaching early markets with attractive, firm-fleshed peaches producers and growers constantly search for improved varieties of peach trees the fruit of which can be harvested and shipped before the expected dates of maturity for crops of varieties having competing consumer acceptance.

ORIGIN OF THE INVENTION

Being a grower well acquainted with the desirability of reaching early markets with fruit which enjoys widespread consumer acceptance, I continuously observe the characteristics of peach varieties grown on my ranch located near Fowler, Calif. in the San Joaquin Valley.

The invention herein claimed is a variety of peach tree which was discovered by me under the following factual circumstances:

Late in the spring of 1971 I was walking through my orchard in which I grow peaches of the Red Top variety, located near 7240 East Lincoln Ave., Fowler, Calif. when a particular tree of the Red Top variety caught my attention. I observed on that tree a limb bearing fruit which appeared to be reaching maturity substantially before the fruit of the rest of the peach trees in the orchard. I continued to follow the fruit produced by that particular limb for another two years and found that each year the fruit produced by that limb matured approximately a week to 10 days earlier than the fruit of all of the rest of the trees of the Red Top variety growing in my orchard.

During the grafting season of 1973 I took bud wood from that limb which I have determined to be a sport limb and grafted it over root stock of the Red Top variety. In 1976 a substantial quantity of fruit was produced from the grafted-over trees and in each instance the fruit produced appeared to have substantially the same appearance and the same quality as the Red Top variety, excepting that the date on which the fruit of the new variety matured was approximately 7 to 10 days ahead of the fruit of the Red Top variety. I have also observed that during the last 3 or 4 weeks preceding maturity, the fruit of the new variety accelerates to maturity and ultimately matures about a week to 10 days earlier than the Red Top peach. Under the soil, water and climatic conditions of the San Joaquin Valley of California in which my orchard is located maturity is reached on or about June 18.

The new variety of peach tree, while having a general resemblance to the Red Top variety (unpatented) is in comparison characterized by the distinction of being ready for market about a week to 10 days earlier than the fruit of the Red Top variety.

BRIEF DESCRIPTION OF THE DRAWING

The drawing comprises a photographic illustration of fruit halved, to expose the flesh thereof, and whole to illustrate the configuration and color of the fruit of the new variety of peach tree.

DESCRIPTION OF THE NEW VARIETY

The following description of the botanical details of the new and distinct variety of peach tree is for the sake of convenience provided with comparisons being made to the Red Top variety which it most nearly resembles, and with color definitions being given with reference made to the Nickerson Color Fan distributed by the American Horticultural Society. The details are as follows:

Tree:
- *Size.*—Large.
- *Productivity.*—Good.
- *Regularity of bearing.*—Appears to be very regular.

Branches:
- *Size and configuration.*—About the same as that of the Red Top variety.
- *Color.*—Strong yellow green (2.5 GY 6/8).
- *Lenticels.*—About the same in number and appearance as the Red Top variety.

Leaves:
- *Size.*—Medium, about the size of the Red Top variety.
- *Length.*—Approximately 5 to 7 inches.
- *Width.*—Approximately 1.8 inches.
- *Form.*—Lanceolate with acuminate tip.
- *Thickness.*—Medium.
- *Glandular characteristics.*—Reniform in shape and located on petiole near base of the blade.
- *Marginal form.*—Crenate.
- *Color.*—Moderate olive green (5 GY 4/3).
- *Flower buds.*—About the same in shape, size and color as that of the Red Top variety.

Flowers: Dates of Bloom, size and color about the same as that of the Red Top variety.

Fruit:

*Maturity.*—Reached in the San Joaquin Valley of California about June 18, and when compared to the Red Top variety grown in the same orchard and under the same conditions about a week to 10 days before the Red Top variety.

*Size.*—Large at maturity.

*Form.*—Uniform and nearly round. The fruit in all respects closely resembles that of the Red Top variety, except that the apex of the new variety tends to be slightly more pronounced than the apex of the fruit of the Red Top variety.

Skin: Thickness, texture, color and pubescence appear to be in all respects, like that of the Red Top variety. Tendency to Crack — slight.

Flesh:

*Color.*—Brilliant yellow (2.5 Y 9/9) streaked with veins of vivid yellow (2.5 Y 8/12) having moderate pink (2.5 R 8/7) veins near pit cavity extending to apex.

*Firmness.*—Firm.

*Quality.*—Fine grained.

*Flavor.*—Good.

*Ripening.*—Even.

*Good eating quality.*

Stone: Freestone similar in size and shape to the stone of the Red Top variety.

Use:

*Shipping, eating and canning characteristics.*—Good.

*Keeping quality.*—Good.

*Shipping quality.*—Very good.

It is to be understood that normal variations in the described characteristics of the new variety peach tree may result from environmental changes, such as in climate and soil conditions, and from changes in cultural practices, such as in pruning, thinning, fertilizing, spraying, irrigating and the like. The preceding description is that of the new variety produced under the ecological conditions prevailing at my farm new Fowler, Calif. and the described characteristics are found to hold true in asexual reproduction of the variety.

Having thus described my new variety of peach tree I claim:

1. The new and distinct variety of peach tree, substantially as shown and described herein, characterized by highly colored, firm, fine grained, yellow-fleshed freestone fruit which reaches maturity a week to 10 days before the peaches of the Red Top variety (unpatented).

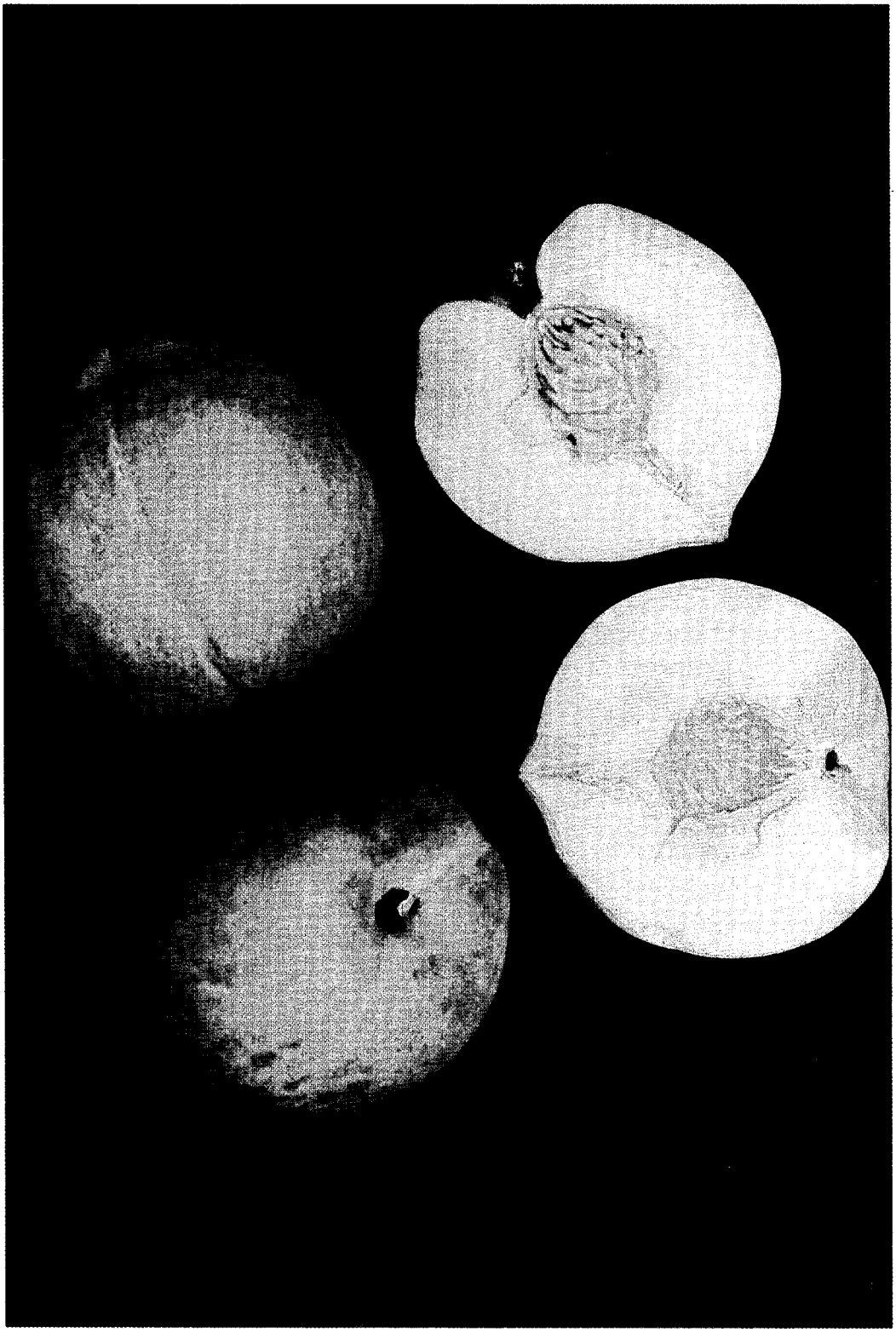

* * * * *